US012797473B2

(12) United States Patent
Kim

(10) Patent No.: US 12,797,473 B2
(45) Date of Patent: Nov. 17, 2026

(54) GLUTEN-FREE MEDICATION AID COMPOSITION FOR COMPANION ANIMALS, AND METHOD FOR MANUFACTURING THE SAME

(71) Applicant: Naturein Co., Ltd., Anyang-si (KR)

(72) Inventor: Jaehyoung Kim, Gwacheon-si (KR)

(73) Assignee: NATUREIN CO., LTD., Anyang-si (KR)

( * ) Notice: Subject to any disclaimer, the term of this patent is extended or adjusted under 35 U.S.C. 154(b) by 226 days.

(21) Appl. No.: 18/802,336

(22) Filed: Aug. 13, 2024

(65) Prior Publication Data

US 2025/0345437 A1 Nov. 13, 2025

(30) Foreign Application Priority Data

May 10, 2024 (KR) ........................ 10-2024-0062197

(51) Int. Cl.

*A61K 47/30* (2006.01)
*A61K 47/10* (2017.01)
*A61K 47/26* (2006.01)
*A61K 47/42* (2017.01)
*A61K 47/44* (2017.01)
*A61K 47/46* (2006.01)

(52) U.S. Cl.

CPC .............. *A61K 47/30* (2013.01); *A61K 47/10* (2013.01); *A61K 47/26* (2013.01); *A61K 47/42* (2013.01); *A61K 47/44* (2013.01); *A61K 47/46* (2013.01)

(58) Field of Classification Search

CPC ........ A61K 47/30; A61K 47/10; A61K 47/26; A61K 47/42; A61K 47/44; A61K 47/46; A61K 9/0056; A61K 9/1652; A61K 9/08; A61K 9/2059; A61K 47/02; A61K 47/36; A23K 10/20; A23K 10/30; A23K 20/105; A23K 20/158; A23K 20/163; A23K 20/174; A23K 40/20; A23K 50/40; A23K 50/42

See application file for complete search history.

(56) References Cited

U.S. PATENT DOCUMENTS

2024/0065293 A1 * 2/2024 Van Eyk ................ A23K 10/30

FOREIGN PATENT DOCUMENTS

| | | | | |
|---|---|---|---|---|
| KR | 10-1999073 | | 7/2019 | |
| KR | 10-20210149519 | | 12/2021 | |
| KR | 20210149519 A | * | 12/2021 | ............ A23K 20/26 |
| WO | 2022150037 A1 | | 7/2022 | |

OTHER PUBLICATIONS

Maddie's American (Ultra Easy Pill-Dough, Maddie's American pet products, Reviews date back to before 2023 (Year: 2023).*
KR-20210149519-A translated (Year: 2021).*
Amazon—Easy Pill Ultra Pet Treat Wrap, Maddie's American Pet Products, Sep. 14, 2022, 9 pages.
KR Office Action for KR10-2024-0062197 dated Nov. 11, 2024, 14 pages.

* cited by examiner

*Primary Examiner* — Robert A Wax
*Assistant Examiner* — John Seungjai Kwon
(74) *Attorney, Agent, or Firm* — Nixon Peabody LLP

(57) ABSTRACT

A gluten-free medication aid composition for companion animals, and a method for manufacturing the same are disclosed. The gluten-free medication aid composition includes bean-type starch and cereal-type starch. The bean-type may include black beans, pinto beans, blue beans, lentil beans, peas, soybeans, chickpeas, white pea beans, or a mixture thereof. The cereal-type starch may include rice, corn, oats, sweet potatoes, potatoes, or tapioca. The gluten-free medication aid composition may further include oil, glycerin, sorbitol, and/or animal protein. A method for manufacturing the gluten-free medication aid composition includes manufacturing a first blend by mixing bean-type starch and oil; adding purified water into the first blend and heating the first blend; manufacturing a second blend by mixing animal protein and food additives with the heated first blend; and heating the second blend and then cooling the heated second blend. Cereal-type starch is added to the first blend or second blend.

20 Claims, 2 Drawing Sheets

| | Exterior | Cohesion |
|---|---|---|
| Embodiment example |  |  |
| Comparison example |  |  |

FIG. 2
PRIOR ART

| Dosage form | Injection method | Use process |
|---|---|---|
| Powder | Use a syringe after stirring into water |  |
| | Capsulize in an empty capsule | 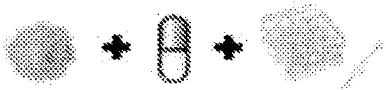 |
| | Inject on the top of mouth after mixing with honey, jam, and others |  |
| | Intake by mixing into canned wet food, churu, and milk |  |
| Capsule pill | Intake by blending with snacks with high preferability and scent | 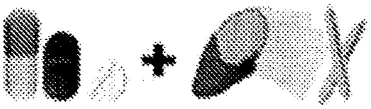 |
| | Intake with medication aid | 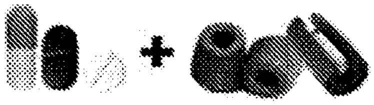 |
| | Direct intake of medicine powder in an empty capsule | 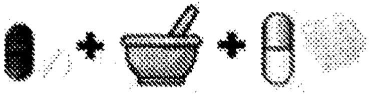 |

GLUTEN-FREE MEDICATION AID COMPOSITION FOR COMPANION ANIMALS, AND METHOD FOR MANUFACTURING THE SAME

CROSS REFERENCE TO RELATED APPLICATION

This application claims the priority of Korean Patent Application No. 10-2024-0062197, filed with the Korean Intellectual Property Office on May 10, 2024, which is incorporated herein by reference in its entirety.

TECHNICAL FIELD

The present invention is directed to a gluten-free medication aid composition for companion animals, and a method for manufacturing the same.

BACKGROUND ART

There are a growing number of aged people and people living alone, with the market for companion animals growing exponentially; thus, products or services related to companion animals are becoming a new promising industry.

Pets used to mean an animal bred for pleasure by humans such as dogs or cats living together with them; nowadays, however, pets are called companion animals to include the meaning of existence as friend or family giving psychological stability and closeness by living together and are not considered an item simply for the pleasure of humans.

On the other hand, the increase of aging companion animals and interest in pet care increase, and the number of injectable prescription medications and nutritional supplements is growing, but the method of using conventional injection has various problems (Table 1).

TABLE 1

| Dosage form | Injection method | Use process | Problems |
|---|---|---|---|
| Powder | Use a syringe after stirring into water | See FIG. 2 | Strong resistance (bitter taste, scent)<br>Fear of injecting with syringe<br>Occurrence of bite accident |
| | Capsulize in an empty capsule | See FIG. 2 | Inconvenient to put in an empty capsule |
| | Inject on the top of mouth after mixing with honey, jam, and others | See FIG. 2 | Danger of diabetes caused by excessive sugar, lowers the effect of medicine<br>Indigestive, obesity, excessive weight gain |
| | Intake by mixing into canned wet food, churu, and milk | See FIG. 2 | Lower the effect of medicine and generating stomach acid, intake of high calories and high salt<br>Inconvenience of necessity of bowl, spoon, and chopstick and others |
| Capsule pill | Intake by blending with snacks with high preferability and scent | See FIG. 2 | Preparation process takes time<br>Difficulty of injecting serval folds with high calories |
| | Intake with medication aid | See FIG. 2 | Difficulty of intake caused by exposure to big-sized medicine<br>Difficulty of injection of serval folds with high calories<br>Indigestion and allergy due to gluten composition |

TABLE 1-continued

| Dosage form | Injection method | Use process | Problems |
|---|---|---|---|
| | Direct intake of medicine powder in an empty capsule | See FIG. 2 | Inconvenient to put in an empty capsule |

Specifically, the prescription medicine of companion animals comes in various dosage forms/sizes with various injection methods, and the conventional capsule/pill-type medication aid has problems of the medicine being in a specific size only and being exposed to the outside.

Furthermore, the conventional medication supplement includes a large amount of gluten that triggers allergy, immune reaction, and indigestion and, for some types of animal, paroxysmal dyskinesia, and oil for flexibility and viscosity and conventional medication supplement production has problems of split phenomenon occurring due to heat after getting cluttered into a bulk or exposed to air while being distributed.

Furthermore, the medication supplement is usually for sick and aged animals, so the medication supplement for the companion animal must be reinforced for the companion animal with nutritional recipe, but the conventional medication supplement normally contains a large amount of oil, etc. to keep it moist and prevent evaporation, resulting in the intake of too many unnecessary calories; specifically, it causes problems of rising blood sugar if the supplement is added with corn syrup, fructose, and other related items to increase preferability.

Therefore, it is necessary to develop a convenient medication supplement to shorten the intake preparation time (preparation/injection/organization), mask the unique scent and taste of medicine to enable natural intake without force, and aid in digestion and metabolism with low calories without causing obesity, excessive weight gain, and other related diseases that trigger allergy and indigestion even if taken by many folds.

SUMMARY OF THE INVENTION

The term embodiment and like terms, e.g., implementation, configuration, aspect, example, and option, are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter. This summary is also not intended to be used in isolation to determine the scope of the claimed subject matter. The subject matter should be understood by reference to appropriate portions of the entire specification of this disclosure, any or all drawings, and each claim.

According to certain aspects of the present disclosure, a gluten-free medication aid composition for companion animals includes bean-type starch and cereal-type starch.

In some embodiments, the bean-type includes black beans, pinto beans, blue beans, lentil beans, peas, soybeans, chickpeas, white pea beans, or a mixture thereof.

In some embodiments, the cereal-type starch includes rice, corn, oats, sweet potatoes, potatoes, or tapioca.

In some embodiments, the bean-type starch and cereal-type starch are gelatinized.

In some embodiments, an amount of gluten in the gluten-free medication aid composition is 20 mg/kg (20 ppm) or lower.

In some embodiments, an amount of the bean-type starch in the gluten-free medication aid composition is 15 weight % to 40 weight %, compared to a total weight of the gluten-free medication aid composition.

In some embodiments, the amount of the bean-type starch in the gluten-free medication aid composition is 20 to 40 weight %, 20 to 35 weight %, 25 to 35 weight %, 25 to 34 weight %, 25 to 33 weight %, 26 to 33 weight %, 27 to 33 weight %, 28 to 33 weight %, 29 to 33 weight %, or 30 to 33 weight %, compared to the total weight of the gluten-free medication aid composition.

In some embodiments, a mixture of chickpeas and white pea beans is used for the bean-type starch, and a weight ratio between the chickpeas and the white pea beans in the mixture is 2:1 to 1:2, 2:1 to 1:1.5, 1.5:1 to 1:1.5, or 1.5:1 to 1:1.

In some embodiments, an amount of the cereal-type starch in the gluten-free medication aid composition is 1 weight % to 8 weight %, compared to a total weight of the gluten-free medication aid composition.

In some embodiments, the amount of the cereal-type starch in the gluten-free medication aid composition is 2 to 8 weight %, 3 to 8 weight %, 4 to 8 weight %, 5 to 8 weight %, 2 to 7 weight %, 2 to 6 weight %, 3 to 7 weight %, 4 to 7 weight %, 5 to 7 weight %, 3 to 6 weight %, 4 to 6 weight %, or 5 to 6 weight %, compared to the total weight of the gluten-free medication aid composition.

In some embodiments, the gluten-free medication aid composition further includes oil including vegetable or animal oil.

In some embodiments, the gluten-free medication aid composition further includes glycerin.

In some embodiments, the gluten-free medication aid composition further includes sorbitol.

In some embodiments, the gluten-free medication aid composition further includes animal protein including cheese, chicken, pork, or beef.

According to certain aspects of the present disclosure, a method for manufacturing a gluten-free medication aid composition for companion animals includes S1) manufacturing a first blend by mixing bean-type starch and oil; S2) adding purified water to the first blend and heating the first blend; S3) manufacturing a second blend by mixing animal protein and food additives with the heated first blend; and S4) heating the second blend and then cooling the heated second blend. The method further includes adding cereal-type starch to the first blend between S1 and S2; or adding cereal-type starch to the first blend or second blend at S3.

In some embodiments, an amount of the bean-type starch is 20 to 40 weight %, 20 to 35 weight %, 25 to 35 weight %, 25 to 34 weight %, 25 to 33 weight %, 26 to 33 weight %, 27 to 33 weight %, 28 to 33 weight %, 29 to 33 weight %, or 30 to 33 weight %, compared to a total weight of the gluten-free medication aid composition.

In some embodiments, a gelatinization process is performed by heating after adding the purified water at S2.

In some embodiments, the heating at S2 is performed at 85 degrees Celsius or higher for 20 to 60 minutes.

In some embodiments, an amount of the animal protein at S3 is 11 to 15 weight %, 12 to 15 weight %, 13 to 15 weight %, or 14 to 15 weight %, %, compared to a total weight of the gluten-free medication aid composition.

In some embodiments, the food additives at S3 includes at least one of glycerin, sorbitol, rosemary, or vitamin E.

BRIEF DESCRIPTION OF THE DRAWINGS

The disclosure, and its advantages and drawings, will be better understood from the following description of representative embodiments together with reference to the accompanying drawings. These drawings depict only representative embodiments, and are therefore not to be considered as limitations on the scope of the various embodiments or claims.

FIG. 2 shows images omitted in the column under "Use process" of Table 1.

DETAILED DESCRIPTION

Figure 1:
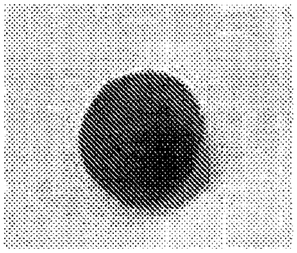
FIG. 1 shows results of evaluation of the exterior and cohesion of the medication aids manufactured as an example according to one embodiment and as a comparative example.
Figure 1:
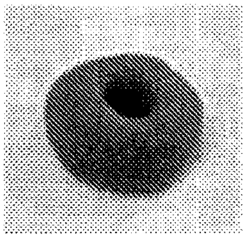
Figure 1:
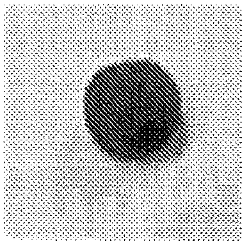
Figure 1:
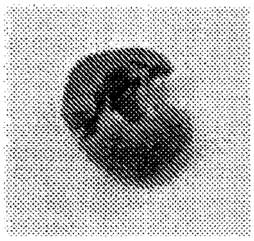

The inventor recognizes the problem of the conventional technology, overcomes the side effect due to intake with convenience of injection of the medication aid including specific composition, and confirms that the medication aid could be useful for injection due to the high preferability among companion animals; thus completing the invention.

The invention is related to a gluten-free medication aid composition for companion animals including bean-type starch and cereal-type starch.

The invention deals with a manufacturing method of gluten-free medication aid for companion animals.

Solutions for the above-identified problems are explained below. All combinations of various elements cited in the present disclosure are included in the range of the invention. Furthermore, the range of invention specifically described below is not limited thereto.

Furthermore, as long as the terminology is not defined in the statement, all terminologies used in the statement should be understood to have the same meaning as those generally understood by a person with general knowledge in the field of technology where the invention belongs.

Furthermore, a single expression includes various expressions as long as the meaning is clearly translated into other meanings in the context.

Term 1, term 2, and other terms in the present disclosure could be used for classifying or explaining one composition element with another composition element, but the composition element by the terms above should not be translated limitedly. For instance, the first composition element in the range of the invention could be named the second composition element or vice versa.

Furthermore, "degree" combined with numbers in the invention is construed as degree Celsius (° C.) and could be used interchangeably with ° C. (for instance, "100 degrees" is considered to have the same meaning as 100° C.).

The present disclosure provides a gluten-free medication aid composition for companion animals including bean-type starch and cereal-type starch.

According to one embodiment of the invention, the bean-type may be black beans, pinto beans, blue beans, lentil beans, peas, soybeans, chickpeas, white pea beans, or a mixture thereof, but not limited thereto.

According to one embodiment of the invention, the bean-type could be chickpeas, white pea beans, or a mixture thereof, but not limited thereto.

According to one embodiment of the invention, the bean-type could be chickpeas and white pea beans, but not limited thereto.

The chickpeas have the scientific name *Cicer arietinum*, regarded as Egyptian beans, and they are bean plants belonging to the bean family. The overall exterior of the seed features a head shape similar to chicks, and the taste of the beans is like marron full of protein. Beans generally grow in the Middle East region and grow well in a dry temperature. Chickpeas are a highly nutritious food rich in protein and fiber with various vitamin and minerals.

The white pea beans may mean one of the types of *Phaseolus vulgaris* grown and cultivated in America. White pea beans are white dried beans with smaller size compared to various other types of white peas whose shape is slightly flat oval.

The bean-type starch in a composition according to one embodiment of the invention could be 15 to 40 weight % compared to the total weight of the overall composition, but not limited thereto.

Furthermore, according to one embodiment of the invention, the bean-type starch could include 20 to 40 weight %, 20 to 35 weight %, 25 to 35 weight %, 25 to 34 weight %, 25 to 33 weight %, 26 to 33 weight %, 27 to 33 weight %, 28 to 33 weight %, 29 to 33 weight %, or 30 to 33 weight % as the ratio against the overall composition, but not limited thereto.

According to one embodiment of the invention, the mixture of chickpeas and white pea beans is used for the bean type, and the ratio between chickpeas and white pea beans could include 2:1 to 1:2, 2:1 to 1:1.5, 1.5:1 to 1:1.5, or 1.5:1 to 1:1 as weight ratio, but not limited thereto.

According to one embodiment of the invention, the cereal-type may be rice, corn, oats, sweet potatoes, potatoes, tapiocas, or a mixture thereof, but not limited thereto.

According to one embodiment of the invention, the cereal-type may be rice or tapioca, but not limited thereto.

The cereal starch in the invention could include 1 to 8 weight % as the ratio against the overall composition, but not limited thereto.

According to one embodiment of the invention, the cereal-type starch may include 2 to 8 weight %, 3 to 8 weight %, 4 to 8 weight %, 5 to 8 weight %, 2 to 7 weight %, 2 to 6 weight %, 3 to 7 weight %, 4 to 7 weight %, 5 to 7 weight %, 3 to 6 weight %, 4 to 6 weight %, or 5 to 6 weight % as the ratio against the overall composition, but not limited thereto.

According to one embodiment of the invention, the cereal-type starch includes the starch that went through a separate process.

"Starch" may be one of the carbohydrates and is a polysaccharide that is a glucoside combination of various glucoses combined.

The starch may be better when it is gluten-free (without gluten). For instance, starches including gluten—which are wheat starch, rye starch, barley, and a mixture thereof—are excluded.

"Gluten-free" means food that does not use wheat, rye, barley, and a combination thereof as ingredients or which reduced the amount of gluten to 20 mg/kg (20 ppm) or lower.

"Gluten" means insoluble protein complex formed after protein is included in the cereal type such as wheat, rye, barley, and other related cereals where gliadin and glutenin are mixed with water.

According to one embodiment of the invention, the bean-type starch and the cereal-type starch may be gelatinized.

"Gelatinization or α-lized" means to get bigger in volume with high viscosity to become sticky, which is a phenomenon that is expanded by heat and moisture when heating starch. The molecules of amylose and amylopectin form a micelle structure inside a particle of starch by hydrogen bond and form starch particles overlapping with starch layers by forming a starch layer with the collected micelles. If this starch is added with water and heated, the regularly micelle structure of starch gets loose due to heat energy with water penetrating, thereby making it bulkier. If this is heated further, the micelle structure is damaged, forming a colloidal solution of starch particles with higher viscosity.

According to one embodiment of the invention, the starch of the composition may be completely gelatinized with heat after adding purified water for 20 minutes at 85° C. or higher. If not, the viscosity is not uniform or the aging process afterwards becomes much faster.

The composition of the invention may further include oil.

According to one embodiment of the invention, the oil may be vegetable or animal oil.

The vegetable oil could be sunflower seed oil, rapeseed oil, soybean oil, coconut oil, peanut oil, or a mixture thereof, but not limited thereto.

The animal oil could be butter, pork fat (lard), beef tallow, or a mixture thereof, but not limited thereto.

According to one embodiment of the invention, the oil could be vegetable oil, but not limited thereto.

Furthermore, according to one embodiment of the invention, the vegetable oil could be sunflower seed oil, but not limited thereto.

According to one embodiment of the invention, the oil may include 1 to 8 weight % as the ratio against the overall composition, but not limited thereto.

According to one embodiment of the invention, the oil could include 2 to 8 weight %, 3 to 8 weight %, 4 to 8 weight %, 5 to 8 weight %, 2 to 7 weight %, 2 to 6 weight %, 3 to 7 weight %, 4 to 7 weight %, 5 to 7 weight %, 3 to 6 weight %, 4 to 6 weight %, or 5 to 6 weight % as the ratio against the overall composition, but not limited thereto.

According to one embodiment of the invention, the composition may further include glycerin.

According to one embodiment of the invention, the glycerin may be included in 10 to 20 weight % as the ratio against the overall composition, but not limited thereto.

Furthermore, according to the various embodiments of the invention, the glycerin may be included in 10 to 19 weight %, 10 to 18 weight %, 10 to 17 weight %, 10 to 16 weight %, 10 to 15 weight %, 11 to 19 weight %, 12 to 19 weight %, 13 to 19 weight %, 14 to 19 weight %, 11 to 18 weight %, 12 to 18 weight %, 13 to 18 weight %, 14 to 18 weight %, 11 to 17 weight %, 12 to 17 weight %, 13 to 17 weight %, 14 to 17 weight %, 11 to 16 weight %, 12 to 16 weight %, 13 to 16 weight %, 14 to 16 weight %, 11 to 15 weight %, 12 to 15 weight %, 13 to 15 weight %, or 14 to 15 weight % as the ratio, but not limited thereto.

According to one embodiment of the invention, the composition may further include more ingredients including animal protein to balance nutrition and increase preferability.

According to one embodiment of the invention, the ingredients including animal protein may be cheese, chicken, pork, or beef, but not limited thereto.

According to various embodiments of the invention, the ingredients including animal protein could be cheese, chicken, or beef, but not limited thereto.

According to various embodiments of the invention, the ingredients including animal protein could be beef, but not limited thereto.

According to one embodiment of the invention, the ingredients including animal protein may be included in 10 to 15 weight % as the ratio, but not limited thereto.

According to various embodiments of the invention, the animal protein may be included in 11 to 15 weight %, 12 to 15 weight %, 13 to 15 weight %, or 14 to 15 weight % as the ratio, but not limited thereto.

Furthermore, according to one embodiment of the invention, the composition may additionally include the component known to increase functionality, preferability, and other functions.

According to one embodiment of the invention, the additional components could be sorbitol, rosemary, vitamin E, and others, but not limited thereto.

In case of including sorbitol in the composition, the sorbitol may be included in 1 to 12 weight % as the ratio against the overall composition, but not limited thereto.

According to various embodiments of the invention, the sorbitol may be included in 2 to 12 weight %, 3 to 12 weight %, 4 to 12 weight %, 5 to 12 weight %, 6 to 12 weight %, 7 to 12 weight %, 8 to 12 weight %, 9 to 12 weight %, 1 to 11 weight %, 2 to 11 weight %, 3 to 11 weight %, 4 to 11 weight %, 5 to 11 weight %, 6 to 11 weight %, 7 to 11 weight %, 8 to 11 weight %, or 9 to 11 weight % as the ratio against the overall composition, but not limited thereto.

The companion animals in the present disclosure are not specifically limited if the animals could live with humans. For instance, the animals could include dogs, cats, rabbits, pigs, parrots, hamsters, and other related animals, but dogs or cats can be preferred with dogs more preferred, but not limited thereto.

The composition according to various embodiments of the invention could be manufactured into an adequate dosage form notified. For instance, the composition could be molded or prepared in a specific shape that can be injected as injection medication or prepared into a paste type for customers to use the composition divided as much as they want, but the dosage form is not limited thereto.

The invention provides a method for manufacturing a gluten-free medication aid for companion animals, the method including:

S1) a step of manufacturing a first (1) blend by mixing bean-type starch and oil;

S2) a step of heating after injecting purified water into the first (1) blend;

S3) a step of manufacturing a second (2) blend by mixing animal protein and food additives into the heated first (1) blend; and S4) a step of cooling after heating the second (2) blend.

The method may further include injecting cereal-type starch between steps S1 and S2; or at step S3.

Various embodiments of the manufacturing method are described below.

At step S1, the bean-type starch could form complete distribution by being mixed with oil.

At step S1, the bean-type could be black beans, pinto beans, blue beans, lentil beans, peas, soybeans, chickpeas, white pea beans, or a mixture thereof, but not limited thereto.

According to various embodiments of the invention, the bean-type could be chickpeas, white pea beans, or a mixture thereof, but not limited thereto.

According to one embodiment of the invention, the bean-type could be chickpeas and white pea beans, but not limited thereto.

According to one embodiment of the invention, the bean-type starch of the composition may have 15 to 40 weight % as the ratio against the overall composition, but not limited thereto.

Furthermore, according to various embodiments of the invention, the bean-type starch could include 20 to 40 weight %, 20 to 35 weight %, 25 to 35 weight %, 25 to 34 weight %, 25 to 33 weight %, 26 to 33 weight %, 27 to 33 weight %, 28 to 33 weight %, 29 to 33 weight %, or 30 to 33 weight % as the ratio against the overall composition, but not limited thereto.

According to one embodiment of the invention, the mixture of chickpeas and white pea beans is used for the bean-type, and the ratio between chickpeas and white pea beans is 2:1 to 1:2 weight rate, 2:1 to 1:1.5 weight rate, 1.5:1 to 1:1.5 weight rate, or 1.5:1 to 1:1 weight rate, but not limited thereto.

At step S1, the oil could be vegetable or animal oil.

The vegetable oil could be sunflower seed oil, rapeseed oil, coconut oil, peanut oil, or a mixture thereof, but not limited thereto.

The animal oil could be butter, pork fat (lard), beef tallow, or a mixture thereof, but not limited thereto.

According to one embodiment of the invention, the oil could be vegetable oil, but not limited thereto.

Furthermore, according to one embodiment of the invention, the vegetable oil could be sunflower seed oil, but not limited thereto.

According to one embodiment of the invention, the oil may include having the ratio against the overall composition at 1 to 8 weight %, but not limited thereto.

According to one embodiment of the invention, the oil may be included in 2 to 8 weight %, 3 to 8 weight %, 4 to 8 weight %, 5 to 8 weight %, 2 to 7 weight %, 2 to 6 weight %, 3 to 7 weight %, 4 to 7 weight %, 5 to 7 weight %, 3 to 6 weight %, 4 to 6 weight %, or 5 to 6 weight % as the ratio against the overall composition, but not limited thereto.

At step S2, the gelatinization process is performed by heating after inputting purified water.

At step S2, the heating could be performed at 85 degrees Celsius or higher for 20 to 60 minutes, but not limited thereto.

Step S3 may include a step of injecting animal protein and food additives to the first (1) blend to increase preferability, functionality, and nutrition.

According to one embodiment of the invention, the ingredients including animal proteins could be cheese, chicken, pork, or beef, but not limited thereto.

According to the various embodiments of the invention, the ingredients including animal protein could be cheese, chicken, pork, or beef, but not limited thereto.

According to the various embodiments of the invention, the ingredients including animal protein could be beef, but not limited thereto.

According to one embodiment of the invention, the ingredients including animal protein may be included in 10 to 15 weight %, but not limited thereto.

According to the various embodiments of the invention, the animal protein may be included in 11 to 15 weight %, 12 to 15 weight %, 13 to 15 weight %, or 14 to 15 weight %, but not limited thereto.

At step S3, the food additives could be glycerin, sorbitol, rosemary, vitamin E, and other related items, but not limited thereto.

According to one embodiment of the invention, Glycerin may be included in 10 to 20 weight % as the ratio against the overall composition, but not limited thereto.

Furthermore, according to various embodiments of the invention, the glycerin may be included in 10 to 19 weight %, 10 to 18 weight %, 10 to 17 weight %, 10 to 16 weight %, 10 to 15 weight %, 11 to 19 weight %, 12 to 19 weight %, 13 to 19 weight %, 14 to 19 weight %, 11 to 18 weight %, 12 to 18 weight %, 13 to 18 weight %, 14 to 18 weight %, 11 to 17 weight %, 12 to 17 weight %, 13 to 17 weight %, 14 to 17 weight %, 11 to 16 weight %, 12 to 16 weight %, 13 to 16 weight %, 14 to 16 weight %, 11 to 15 weight %, 12 to 15 weight %, 13 to 15 weight %, or 14 to 15 weight % as the ratio, but not limited thereto.

According to one embodiment of the invention, sorbitol is added at step S3, and the sorbitol may be included in 1 to 12 weight % as the ratio against the overall composition, but not limited thereto.

According to various embodiments of the invention, the sorbitol may be included in 2 to 12 weight %, 3 to 12 weight %, 4 to 12 weight %, 5 to 12 weight %, 6 to 12 weight %, 7 to 12 weight %, 8 to 12 weight %, 9 to 12 weight %, 1 to 11 weight %, 2 to 11 weight %, 3 to 11 weight %, 4 to 11 weight %, 5 to 11 weight %, 6 to 11 weight %, 7 to 11 weight %, 8 to 11 weight %, or 9 to 11 weight % as the ratio against the overall composition, but not limited thereto.

Step S4 is a step of heating and cooling whose heating is at 120° C. or higher for 3 to 5 minutes, but not limited thereto.

The cooling in step S4 could be performed at 10 to 30° C., but not limited thereto.

Furthermore, the cooling could be performed for 3 hours or more, preferably for 3 to 10 hours, but not limited thereto.

According to one embodiment of the invention, the cereal-type starch is injected and mixed between step S1 and step S2; or at step S3.

According to one embodiment of the invention, the cereal-type starch includes separately processed starch. For an instance of the processed starch, the starch could be prepared after being gelatinized or processed for controlling viscosity, but not limited thereto.

According to one embodiment of the invention, the cereal-type could be rice, corn, oats, sweet potatoes, potatoes, tapioca, or a mixture thereof, but not limited thereto.

According to one embodiment of the invention, the cereal-type could be rice or tapioca, but not limited thereto.

According to one embodiment of the invention, the cereal-type starch may include 1 to 8 weight % as the ratio against the overall composition, but not limited thereto.

According to one embodiment of the invention, the cereal-type starch may be included in 2 to 8 weight %, 3 to 8 weight %, 4 to 8 weight %, 5 to 8 weight %, 2 to 7 weight %, 2 to 6 weight %, 3 to 7 weight %, 4 to 7 weight %, 5 to 7 weight %, 3 to 6 weight %, 4 to 6 weight %, or 5 to 6 weight % as the ratio against the overall composition, but not limited thereto.

The specific content related to the manufacturing method in the present disclosure is applied similarly to the composition unless contrary content is mentioned in the disclosure.

The medication aid according to various embodiments of the invention is convenient in terms of shortening the preparation time of injection and smooth enough with adequate viscosity to swallow through the throat of the companion animals; hiding the pill is also easy, enabling natural injection without forcing the companion animals.

Furthermore, the medication aid according to various embodiments of the invention could be manufactured into a gluten-free product so as not to cause problems such as allergy, indigestion, or other problems due to gluten.

Furthermore, the medication aid according to various embodiments of the invention has low calories and high preferability among companion animals without any separate high-calorie food so as not to cause problems such as obesity, excessive weight gain, and other problems.

Furthermore, the medication aid according to various embodiments of the invention could help promote the health of the companion animals by containing a component that aids in digestion, metabolism, and others.

The effects that could be obtained by the various embodiments described herein are not limited to the effects mentioned above, and those other effects could be understood clearly by a person with general knowledge in the technical field based on the specific explanation below.

The following examples or embodiments are intended to explain the example of the invention, and the range of the invention is not limited to thereto. Furthermore, each element or feature could be considered selectively without any clear separate notification. Each element or feature could be in a form that is not combined with other elements or features. Moreover, some elements and/or features combined could constitute various embodiments or examples. Part of the elements and features of some embodiments or examples could be included into other embodiments or examples or could be exchanged with the elements and features corresponding to other embodiments or examples. Furthermore, the terminology not particularly defined in the present disclosure should be understood with the meanings generally used in the technical field where the invention belongs.

Embodiment

After injecting and mixing chickpea starch (powder) and white pea bean starch (powder) in a container, mix with sunflower seed oil in the container.

Then, mix with tapioca starch.

Then, uniformly mix with purified water and gelatinize the mixture by heating at 85° C. or higher.

Then, add and mix with functional ingredients such as flavor, pumpkin powder, animal ingredient, tapioca starch, and vitamin for preferability.

Then, mix well with D-sorbitol.

Sterilize the solid ingredient by steaming at 120 to 140° C. for 1 to 10 minutes (the mixed solid ingredient takes more time to sterilize when the amount becomes larger. A large amount could take more time to sterilize.)

Then, cool the mixture slowly at 10 to 30° C.

Then, put the cooled dough into a molding equipment and mold into a round-sized mixture that is easily consumable by the companion animal.

The composition manufactured according to one embodiment described above is as shown below.

TABLE 2

| Ingredient | Content (weight %) |
|---|---|
| Chickpea | 18.4 |
| White pea beans | 12.5 |
| Sunflower seed oil | 4.7 |
| Tapioca starch | 5.5 |

TABLE 2-continued

| Ingredient | Content (weight %) |
|---|---|
| Purified water | 18.0 |
| Glycerin | 16.0 |
| Sorbitol | 10.3 |
| Rosemary | 0.1 |
| Animal protein | 14.5 |
| Total | 100.0 |

Comparative Example 1

After injecting and mixing chickpea starch (powder) and white pea bean starch (powder) in a container, mix with sunflower seed oil.

Then, mix with tapioca starch.

Then, uniformly mix with purified water.

Then, add and mix with functional ingredients such as flavor, pumpkin powder, animal ingredient, tapioca starch, and vitamin for preferability.

Then, mix well with D-sorbitol.

Sterilize the solid ingredient by steaming at 120 to 140° C. for 1 to 10 minutes (the mixed solid ingredient takes more time to sterilize when the amount becomes larger. A large amount could take more time to sterilize.)

Then, cool the mixture slowly at 10 to 30° C.

Then, put the cooled dough into a molding equipment and mold into a round-sized mixture that is easily consumable by the companion animal.

The composition of comparative example manufactured according to the above described method is as shown below.

TABLE 3

| Ingredients | Content (weight %) |
|---|---|
| Chickpea | 18.4 |
| White pea beans | 12.5 |
| Sunflower seed oil | 5.2 |
| Tapioca starch | 5.5 |
| Purified water | 17.5 |
| Glycerin | 14.5 |
| Sorbitol | 11.8 |
| Rosemary | 0.1 |
| Animal protein | 14.5 |
| Total | 100.0 |

Experimental Example 1

Exterior and Cohesion Test

A cohesion test is conducted to test the exterior after molding the embodiments example and comparative example and test the adequacy as a medication aid.

To use the medication aid according to various embodiments of the invention as powder, refinement, or capsule, processing forming a space to make into powder, refinement, or sealing into a capsule by using a tool on the center part of the complete product following modification. At this time, the sealed refinement or capsule could be exposed from the inside if crack or breakage occurs on the product while forming a space, resulting in lower preferability among companion animals, so the inconvenience of the user of the medication aid could increase.

The results of the exterior and cohesion test are shown in FIG. 1.

As shown in FIG. 1, the comparative example 1 is confirmed to have low adequacy as a medication aid due to being cracked or completely destroyed.

Experimental Example 2

(1) Preferability Test 1

The preferability test is performed by dog type and age for a total of 5, and the results are shown in Table 4.

TABLE 4

| Fre-quency | Dog type | Age | Preferability by type (rank) Chicken | Cheese | Beef | Overall preferability |
|---|---|---|---|---|---|---|
| 1 | Poodle | 8 years | 3 | 2 | 1 | Well-eaten |
| 2 | Poodle | 8 years | 2 | 1 | 3 | Well-eaten |
| 1 | Boston terrier | 6 years | 2 | 3 | 1 | Well-eaten |
| 1 | Maltese | 2 years | 1 | 3 | 2 | Well-eaten |
| 2 | Maltese | 2 years | 3 | 2 | 1 | Well-eaten |
| 1 | Maltipoo | 9 months | 1 | 2 | 3 | Well-eaten |
| 2 | Maltipoo | 9 months | 3 | 2 | 1 | Well-eaten |
| 1 | Poodle | 6 years | 3 | 1 | 2 | Well-eaten |
| 2 | Poodle | 6 years | 3 | 1 | 2 | Well-eaten |

As a result, in terms of preferability by type, preferability had differences in order of beef, cheese, and chicken, and overall preferability was high in terms of eating quickly without rejecting by scent, texture, and strength or without neglecting.

(2) Preferability Test 2

A preferability test is carried out after injecting a pill into the medication aid to check the use of the medication aid, and the results are shown in Table 5.

TABLE 5

| Fre-quency | Dog type | Age | Preferability per type (rank) Cheese | Beef | Barbecue | Overall preferability |
|---|---|---|---|---|---|---|
| 1 | Poochon | 6 | 2 | 1 | 3 | Well-eaten |
| 2 | Poochon | 6 | 3 | 2 | 1 | Well-eaten |
| 1 | Yorkshire terrier | 13 | 1 | 2 | 3 | Well-eaten |
| 2 | Yorkshire terrier | 13 | 3 | 1 | 2 | Well-eaten |
| 1 | Shih tzu | 13 | 1 | 2 | 3 | Well-eaten |
| 2 | Shih tzu | 13 | 3 | 1 | 2 | Well-eaten |
| 1 | Pomeranian | 7 | 3 | 1 | 2 | Well-eaten |
| 2 | Pomeranian | 7 | 3 | 2 | 1 | Well-eaten |
| 1 | Poodle | 2 | 2 | 1 | 3 | Well-eaten |
| 2 | Poodle | 2 | 3 | 1 | 2 | Well-eaten |
| 1 | Pomeranian | 2 | 1 | 2 | 3 | Well-eaten |
| 2 | Pomeranian | 2 | 1 | 2 | 3 | Well-eaten |
| 1 | Border collie | 5 | 3 | 2 | 1 | Well-eaten |
| 2 | Border collie | 5 | 3 | 2 | 1 | Well-eaten |
| 1 | Maltese | 8 | 3 | 2 | 1 | Well-eaten |
| 2 | Maltese | 8 | 3 | 1 | 2 | Well-eaten |
| 1 | Pomeranian | 2 | 1 | 3 | 2 | Well-eaten |
| 2 | Pomeranian | 2 | 1 | 2 | 3 | Well-eaten |
| 1 | Welsh corgi | 3 | 3 | 1 | 2 | Well-eaten |
| 2 | Welsh corgi | 3 | 3 | 2 | 1 | Well-eaten |
| 1 | Pomeranian | 7 | 3 | 1 | 2 | Well-eaten |
| 2 | Pomeranian | 7 | 3 | 1 | 2 | Well-eaten |
| 1 | Bichon | 10 | 1 | 2 | 3 | Well-eaten |
| 2 | Bichon | 10 | 3 | 2 | 1 | Well-eaten |
| 1 | Bichon | 10 | 3 | 1 | 2 | Well-eaten |
| 2 | Bichon | 10 | 3 | 2 | 1 | Well-eaten |
| 1 | Bichon | 9 | 1 | 2 | 3 | Well-eaten |
| 2 | Bichon | 9 | 1 | 2 | 3 | Well-eaten |
| 1 | Poodle | 8 | 1 | 2 | 3 | Well-eaten |

TABLE 5-continued

| Fre-quency | Dog type | Age | Preferability per type (rank) Cheese | Beef | Barbecue | Overall preferability |
|---|---|---|---|---|---|---|
| 2 | Poodle | 8 | 1 | 2 | 3 | Well-eaten |
| 1 | Mix | 5 | 3 | 1 | 2 | Well-eaten |
| 2 | Mix | 5 | 3 | 1 | 2 | Well-eaten |
| 1 | Mix | 3 | 3 | 2 | 2 | Well-eaten |
| 2 | Mix | 3 | 3 | 2 | 2 | Well-eaten |
| 1 | Pomeranian | 3 | 3 | 1 | 2 | Well-eaten |
| 2 | Pomeranian | 3 | 3 | 1 | 2 | Well-eaten |

In reviewing the results related to preferability by type, there was a difference in preferability—shown as beef, cheese, and barbecue in order—and overall preferability was high because the companion animals have eaten within 20 seconds without refusing or neglecting based on scent, texture, and strength.

In particular, the medication aid of the invention was soft and chewy-type dosage form to cover the pill, which was effective for the companion dog to eat without refusal of the scent of medicine.

Furthermore, in case of beef in particular, the companion animal wandered around or licked the cover, wanting more after the sample was given.

In other words, the inventive medication aid is determined to record a high satisfactory level of the companion dog and the companion by satisfying both preferability and convenience.

The gluten-free medication aid composition can be used conveniently, shortening preparation time for administration or feeding. The gluten-free medication aid composition has adequate viscosity, allowing easy swallowing through the throat of the companion animals. Further, pills can be easily hidden in the gluten-free medication aid composition, allowing natural administration without forcing the companion animal. By being a gluten-free product, problems such as allergy and indigestion can be avoided. Further, the gluten-free medication aid composition has low calories, thus, not causing problems such as obesity, excessive weight gain, and other diseases.

The various embodiments or examples described above could be specified in other specific forms within the range of the technical idea and essential features. Therefore, the explanation provided should not be understood in all aspects but should be considered as one example. The range of various embodiments or examples should be determined by the rational translation of claims attached, and all the changed details within the equivalent range of the various embodiments or examples should be included in the range of the various embodiments or examples. Furthermore, the embodiment or example could be constituted by combining the claims with irrelevant relations of clear citation in the patent claim range or included as a new claim by modifying after the application.

What is claimed is:

1. A gluten-free medication aid composition for companion animals comprising bean-type starch and cereal-type starch, wherein:

the bean-type starch and cereal-type starch are gelatinized such that viscosity is uniform;

the bean-type starch is a mixture of chickpea starch and white pea bean starch;

a weight ratio between the chickpea starch and the white pea bean starch in the mixture is 1.5:1 to 1:1;

the cereal-type starch is tapioca starch;

an amount of gluten in the gluten-free medication aid composition is 20 mg/kg (20 ppm) or lower.

2. The gluten-free medication aid composition of claim 1, wherein an amount of the bean-type starch in the gluten-free medication aid composition is 15 weight % to 40 weight %, compared to a total weight of the gluten-free medication aid composition.

3. The gluten-free medication aid composition of claim 2, wherein the amount of the bean-type starch in the gluten-free medication aid composition is 20 to 40 weight %, 20 to 35 weight %, 25 to 35 weight %, 25 to 34 weight %, 25 to 33 weight %, 26 to 33 weight %, 27 to 33 weight %, 28 to 33 weight %, 29 to 33 weight %, or 30 to 33 weight %, compared to the total weight of the gluten-free medication aid composition.

4. The gluten-free medication aid composition of claim 2, wherein an amount of the cereal-type starch in the gluten-free medication aid composition is 1 weight % to 8 weight %, compared to the total weight of the gluten-free medication aid composition.

5. The gluten-free medication aid composition of claim 4, wherein the amount of the cereal-type starch in the gluten-free medication aid composition is 2 to 8 weight %, 3 to 8 weight %, 4 to 8 weight %, 5 to 8 weight %, 2 to 7 weight %, 2 to 6 weight %, 3 to 7 weight %, 4 to 7 weight %, 5 to 7 weight %, 3 to 6 weight %, 4 to 6 weight %, or 5 to 6 weight %, compared to the total weight of the gluten-free medication aid composition.

6. The gluten-free medication aid composition of claim 1, further comprising oil including vegetable or animal oil.

7. The gluten-free medication aid composition of claim 1, further comprising glycerin.

8. The gluten-free medication aid composition of claim 1, further comprising sorbitol.

9. The gluten-free medication aid composition of claim 1, further comprising animal protein including cheese, chicken, pork, or beef.

10. A method for manufacturing a gluten-free medication aid composition for companion animals, the method comprising:

S1) manufacturing a first blend by mixing bean-type starch and oil, wherein the bean-type starch is a mixture of chickpea starch and white pea bean starch, and a weight ratio between the chickpea starch and the white pea bean starch in the mixture is 1.5:1 to 1:1;

S2) adding purified water to the first blend and heating the first blend;

S3) manufacturing a second blend by mixing animal protein and food additives with the heated first blend; and S4) heating the second blend and then cooling the heated second blend, wherein the method further comprises adding tapioca starch to the first blend between S1 and S2; or adding tapioca starch to the first blend or second blend at S3, and wherein a mixture of the bean-type starch and the tapioca starch is heated at 85° C. or at a higher temperature such that the bean-type starch and tapioca starch are gelatinized.

11. The method of claim 10, wherein an amount of the bean-type starch is 20 to 40 weight %, 20 to 35 weight %, 25 to 35 weight %, 25 to 34 weight %, 25 to 33 weight %, 26 to 33 weight %, 27 to 33 weight %, 28 to 33 weight %, 29 to 33 weight %, or 30 to 33 weight %, compared to a total weight of the gluten-free medication aid composition.

12. The method of claim 10, wherein a gelatinization process to gelatinize the bean-type starch and tapioca starch is performed by heating after adding the purified water at S2.

13. The method of claim 12, wherein the heating at S2 is performed at 85 degrees Celsius or higher for 20 to 60 minutes.

14. The method of claim 10, wherein an amount of the animal protein at S3 is 11 to 15 weight %, 12 to 15 weight %, 13 to 15 weight %, or 14 to 15 weight %, %, compared to a total weight of the gluten-free medication aid composition.

15. The method of claim 10, wherein the food additives at S3 includes at least one of glycerin, sorbitol, rosemary, or vitamin E.

16. The gluten-free medication aid composition of claim 1, wherein:

an amount of the bean-type starch in the gluten-free medication aid composition is 20 weight % to 40 weight %, compared to a total weight of the gluten-free medication aid composition; and an amount of the cereal-type starch in the gluten-free medication aid composition is 1 weight % to 8 weight %, compared to the total weight of the gluten-free medication aid composition.

17. The gluten-free medication aid composition of claim 16, further comprising:

vegetable oil including sunflower seed oil, rapeseed oil, soybean oil, coconut oil, peanut oil, or a mixture thereof; and/or animal oil including butter, pork fat (lard), beef tallow, or a mixture thereof.

18. The gluten-free medication aid composition of claim 17, wherein the vegetable oil is sunflower seed oil.

19. The gluten-free medication aid composition of claim 18, further comprising sorbitol and glycerin.

20. The gluten-free medication aid composition of claim 19, wherein:

an amount of sorbitol in the gluten-free medication aid composition is 9 to 11 weight %, compared to the total weight of the gluten-free medication aid composition;

an amount of glycerin in the gluten-free medication aid composition is 10 to 19 weight %, compared to the total weight of the gluten-free medication aid composition; and an amount of the vegetable oil in the gluten-free medication aid composition is 1 to 8 weight %, compared to the total weight of the gluten-free medication aid composition.

* * * * *